United States Patent [19]

Manghisi et al.

[11] 4,235,904

[45] Nov. 25, 1980

[54] 4-ARYL-5-PIPERAZINOALKYL-1,3-DIOXOL-2-ONES, AND COMPOSITIONS

[75] Inventors: Elso Manghisi; Giuseppe Cascio, both of Monza; Giancarlo Fregnan, Milan; Roberto Porta, Cernobbio, all of Italy

[73] Assignee: Instituto Luso Farmaco d'Italia S.p.A., Milan, Italy

[21] Appl. No.: 16,135

[22] Filed: Mar. 1, 1979

[30] Foreign Application Priority Data

Mar. 3, 1978 [IT] Italy .................................. 20841 A/78
Feb. 14, 1979 [IT] Italy .................................. 48004 A/79

[51] Int. Cl.³ .................. C07D 405/06; C07D 405/14; A61K 31/505; A61K 31/495

[52] U.S. Cl. .................................. 424/251; 424/250; 544/331; 544/360; 544/379

[58] Field of Search .................. 544/379, 331, 360; 424/250, 251

[56] References Cited

U.S. PATENT DOCUMENTS

4,123,529  10/1978  Verge et al. ......................... 544/379

Primary Examiner—Henry R. Jiles
Assistant Examiner—R. W. Ramsuer
Attorney, Agent, or Firm—Bucknam and Archer

[57] ABSTRACT

The invention provides novel 4-aryl-5-aminoalkyl-1,3-dioxol-2-ones having hypocholesterolemic, hypolipemic, antiulcer, antihistaminic and antiserotoninic activities.

25 Claims, No Drawings

4-ARYL-5-PIPERAZINOALKYL-1,3-DIOXOL-2-ONES, AND COMPOSITIONS

This invention concerns a series of compounds having general formula (I)

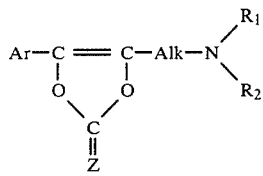

In this formula, Ar represents a carbocyclic arylic group, in particular a monocarbocyclic arylic group such as phenyl, or phenyl substituted one or more times with equal or different substituents such as lower alkyl, trifluoromethyl, lower alkoxy, lower alkenyloxy, lower alkylenedioxy, halogen, alkylmercapto, nitro, amino, lower N,N-dialkylamino.

The carbocyclic arylic residue, moreover, may be a bicyclic group such as biphenyl, naphthyl or naphthyl substituted with one or more equal or different substituents; the substituted naphthylic groups may be, for instance, alkylnaphthyl, trifluoromethylnaphthyl, alkoxynaphthyl, alkenyloxynaphthyl, halogennaphthyl, aminonaphthyl and so on.

Always in formula (I), Alk represents an alkylene group including 1 to 3 carbon atoms; whereas

represents an amino disubstituted group such as N,N-dialkylamino, N-cycloalkyl-N-alkylamino (where cycloalkyl has 3 to 8 carbon atoms), N-lower alkyl-N-phenylalkylamino.

The

group may also be an N,N-alkylene-imino group where alkylene has 4 to 6 carbon atoms, a 4-phenyl substituted N,N-alkylene-imino group, a 4,4-disubstituted N,N-alkylene-imino, such as 7,12-dioxa-3-azaspiro[5,6]dodec-3-yl or 3-azaspiro[5,5]undecan-3-yl; 4-(4-chlorophenyl)-1,2,3,6-tetrahydropyridino; N,N-oxa-alkylene-imino, where alkylene preferably has 4 carbon atoms; N,N-thia-alkylene-imino, where alkylene preferably has 4 carbon atoms; or N,N-azaalkylene-imino, where alkylene has 4 to 6 carbon atoms, which may be linear or branched, and where tha "aza" nitrogen may carry substituents such as lower alkyl or lower alkoxyalkyl, lower acyloxyalkyl, lower arylalkyl, lower diarylalkyl (where aryls preferably are phenyls which may, on their turn, carry substituents such as halogen atoms or lower alkoxy groups), or monocarbocyclic aryl, preferably phenyl, substituted or not with one or more halogen atoms or with lower alkyl, trifluoromethyl, lower alk- oxy; or, finally, an etherocyclic mono cyclic aryl; Z represents oxygen or sulphur.

The invention also concerns the processes for the preparation of the substances with general formula (I).

Finally, the invention concerns pharmaceutical compositions having hypocholesterolemic, hypolipemic, antiulcer, antihistaminic and antiserotoninic activity, which contain, as active principles, one or more compounds with formula (I) or their pharmaceutically acceptable salts.

The compounds (I) may be obtained reacting compounds of general formula (II)

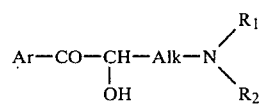

where Ar, Alk and

have the above meanings, with phosgene, thiophosgene, ethyl chlorocarbonate, trichloromethyl chlorocarbonate, ethyl carbonate, eventually in presence of proton acceptors (triethylamine, dimethylaniline and so on) in non polar solvents (choroform, benzene, toluene and so on) and at temperatures ranging from −10° C. to +50° C., or with 1,1-carbonyldiimidazol in non polar solvents (benzene, toluene, 2-butanone) at the solvent boiling temperature, for a few hours.

For the synthesis of the compounds having general formula II, see the methods reported in C.A. 80, 27292 k (1974), which mainly consist in reacting compounds of general formula (III)

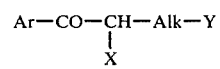

where X and Y represent halogen atoms (while Ar and Alk have the above reported meanings), with alkoxydes of alkali and alkali-earth metals and subsequently with amines with formula

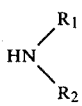

where $NR_1R_2$ have the above reported meanings.

From the compounds of general formula (I) it is possible to prepare salts with pharmaceutically acceptable inorgenic acids, for instance hydrochloric, hydrobromic, nitric, sulphuric, phosphoric acid and so on; as well as with carboxylic organic acids, for instance acetic, propionic, glycolic, malonic, succinic, maleic, hydroxymaleic, fumaric, malic, tarta ric, citric, glucuronic, benzoic, mandelic, salicyclic, 4-aminosalicylic, 2-phenoxybenzoic, 2-acetoxybenzoic, pamoic, nicotinic, isonicotinic acid and so on; or with sulphonic organic acids, for instance methanesulphonic, ethanesulphonic, 2-hydroxy-ethanesulphonic, ethane-1,2- disulphonic, p-toluenesulphonic, naphthalin-2-sulphonic acid and so on.

Mono or poli salts are obtained depending on the salifyable groups present in the molecules.

The products having general formula (I) and their pharmaceutically acceptable salts are endowed with strong hypocholesterolemic and hypolipemic activities, as well as with anti ulcer, antihistaminic and antiserotoninic activities.

They may be administered by oral or rectal route, or injected, in suitable pharmaceutical formulations in solid or liquid form or in suspension (tablets, capsules, ampoules, syrups, suppositories, and so on).

The following tables report, as not limiting examples, the pharmacological characteristics of some compounds described in this application; these compounds are indicated by numbers which have the following meanings:

no. 1: 4-(4-fluorophenyl)-5-[2-(4-phenyl-1-piperazinyl)ethyl]-1,3-dioxol-2-one dihydrochloride no. 2: 4-(4-fluorophenyl)-5-[2-(N-methyl-N-2-phenylethylamino)ethyl]-1,3-dioxol-2-one hydrochloride no. 3: 4-(4-fluorophenyl)-5-[2-(4-(2-pyridyl)-1-piperazinyl)ethyl]-1,3-dioxol-2-one dihydrochloride no. 4: 4-(4-fluorophenyl)-5-[2-(4-methyl-1-piperazinyl)ethyl]-1,3-dioxol-2-one dihydrochloride no. 5: 4-(4-fluorophenyl)-5-[2-(4-(2-methoxyphenyl)-1-piperazinyl)ethyl]-1,3-dioxol-2-one dihydrochloride no. 6: 4-phenyl-5-[2-(4-phenyl-1-piperazinyl)ethyl]-1,3-dioxol-2-one dihydrochloride no. 7: 4-(4-chlorophenyl)-5-[2-(4-phenyl-1-piperazinyl)ethyl]-1,3-dioxol-2-one dihydrochloride no. 8: 4-(4-fluorophenyl)-5-[2-(1-morpholinyl)ethyl]-1,3-dioxol-2-one hydrochloride no. 9: 4-(4-tolyl)-5-[2-(4-phenyl-1-piperazinyl)ethyl]-1,3-dioxol-2-one hydrochloride no. 10: 4-(4-fluorophenyl)-5-[2-(4-(3,5-dichlorophenyl)-1-piperazinyl)ethyl]-1,3-dioxol-2-one hydrochloride no. 11: 4-(4-fluorophenyl)-5-[2-(4-(4-chlorophenyl)-3-methyl-1-piperazinyl)ethyl]-1,3-dioxol-2-one dihydrochloride no. 12: 4-(4-fluorophenyl)-5-[2-(4-(2,5-dichlorophenyl)-1-piperazinyl)ethyl]-1,3-dioxol-2-one hydrochloride no. 13: 4-(4-fluorophenyl)-5-[2-(4-(3,4-dichlorophenyl)-1-piperazinyl)ethyl]-1,3-dioxol-2-one hydrochloride no. 14: 4-(2-naphtyl)-5-[2-(4-phenyl-1-piperazinyl)ethyl]-1,3-dioxol-2-one hydrochloride no. 15: 4-(4-methoxyphenyl)-5-[2-(4-phenyl-1-piperazinyl)ethyl]-1,3-dioxol-2-one dihydrochloride no. 16: 4-(4-methylthiophenyl)-5-[2-(4-phenyl-1-piperazinyl)ethyl]-1,3-dioxol-2-one dihydrochloride no. 17: 4-(4-fluorophenyl)-5-[2-(3-azaspiro[5,5]undecan-3-yl)ethyl]-1,3-dioxol-2-one hydrochloride no. 18: 4-(4-chlorophenyl)-5-[2-(4-(4-chlorobenzhydryl)-1-piperazinyl)ethyl]-1,3-dioxol-2-one dihydrochloride no. 19: 4-(4-chlorophenyl)-5-[2-(4-(2-pyrimidinyl)-1-piperazinyl)ethyl]-1,3-dioxol-2-one maleate no. 20: 4-(4-fluorophenyl)-5-[3-(4-phenyl-1-piperazinyl)propyl]-1,3-dioxol-2-one hydrochloride no. 21: 4-(4-chlorophenyl)-5-[2-(4- chlorophenyl)-1-piperazinyl)ethyl]-1,3-dioxol-2-one hydrochloride no. 22: 4-(4-chlorophenyl)-5-[2-(4-phenyl-1-piperidinyl)ethyl]-1,3-dioxol-2-one hydrochloride no. 23: 4-(4-chlorophenyl)-5-[2-(4-benzhydryl-1-piperazinyl)ethyl]-1,3-dioxol-2-one hydrochloride The toxicity of the compounds, according to the invention, is reported in tables 1, 2 and 3, which also contain the values of hypolipemic, hypocholesterolemic and antiulcer activities respectively, obtained according to the methods described hereunder.

(a) Hypolipemic activity

It has been evaluated orally in rats treated five times in 4 days (once daily during the first three days, twice daily on the fourth day) with the drugs under study. The animals, kept on an empty stomach, were killed on the fifth day, 18 hours after the last treatment. The following tests were carried out:
determination of plasmatic cholesterol The technique described by J. P. Blomhoff (Clin.-Chim.Acta, 43,247, 1973) for the gas-chromatographic determination of total cholesterol was followed. 0,5 ml of the animal serum are hydrolysed at 50° C. for 1 hour with 5 ml of 2% alcoholic KOH. Cholesterol is extracted with 2% petroleum ether at 60°-80° C. and the gas-chromatographic analysis is carried out on the extract with cholesterol acetate as internal standard. The plasmatic cholesterol concentration of the treated animals is evaluated by comparing it with that of the controls. The calculated $ED_{30}$ represents the dose which reduces by 30% the content of plasmatic cholesterol.
determination of plasmatic triglycerides The technique of M. Eggstein (Klin.Nachr.,44, 267, 1966) is used; it consists in determining, by enzymatic route, the total glycerol made free by hydrolysis of the seric neutral fats. In particular, the "Biochemia Test Combination" (Boehringer Mannheim GMBH) was used.

In this case, too, the seric concentration of triglycerides in the treated animals was compared with that in the controls. The calculated $ED_{30}$ represents the dose which reduces by 30% the content of plasmatic triglycerides.

(b) Antiulcer activity in the rat

The method described by Rossi et al. (Comp.Rend.Soc.Biol., 150, 2124, 1956) was followed: 30 minutes after the oral treatment with the drugs under study, the animals, kept on an empty stomach for 48 hours, were immobilized for a period of 4 hours. At the end of this time, the presence of ulcers is checked after killing the animals by ether. The calculated $ED_{30}$ represents the dose which protects 30% of the animals from ulcers.

TABLE 1

| Compound no. | Acute toxicity, $DL_{50}$ (mice) mg/kg ip | Hypocholesterolemic activity, $DE_{30}$ (rats) mg/kg os |
|---|---|---|
| 1 | 420 | 10 |
| 3 | 350 | 25 |
| 6 | 500 | 20 |
| 7 | 650 | 6 |
| 9 | >1000 | 15 |
| 14 | 830 | 20 |
| 19 | 375 | 30 |
| 20 | >500 | 30 |

TABLE 2

| Compound no. | Acute toxicity $DL_{50}$ (mice) mg/kg ip | Hypotriglyceremic activity $DE_{30}$ (rats) mg/kg os |
|---|---|---|
| 1 | 420 | 50 |
| 6 | 500 | 30 |
| 7 | 650 | 30 |
| 9 | >1000 | 100 |
| 10 | >1000 | 100 |

TABLE 2-continued

| Compound no. | Acute toxicity DL$_{50}$ (mice) mg/kg ip | Hypotriglyceremic activity DE$_{30}$ (rats) mg/kg os |
|---|---|---|
| 11 | 1000 | 30 |
| 12 | 1000 | 30 |
| 13 | 600 | 25 |
| 14 | 830 | 100 |
| 15 | >1000 | 20 |
| 16 | >1000 | 100 |
| 17 | 190 | 30 |
| 18 | >1000 | 20 |
| 20 | >500 | 15 |
| 21 | >1000 | 100 |
| 22 | 750 | 50 |
| 23 | >1000 | 100 |

TABLE 3

| Compound no. | Acute toxicity DL$_{50}$ (mice) mg/kg ip | Antiulcer activity DE$_{30}$ (rats) mg/kg os |
|---|---|---|
| 1 | 420 | 10 |
| 2 | 175 | 15 |
| 4 | 300 | 20 |
| 5 | 350 | 30 |
| 6 | 500 | 20 |
| 7 | 650 | 80 |
| 8 | >1000 | 30 |
| 9 | >1000 | 10 |
| 10 | >1000 | 50 |
| 11 | 1000 | 100 |
| 13 | 600 | 100 |

The following examples illustrate the invention without restricting it. The melting and boiling points are not correct. The identity and purity of the substances were checked by means of elemental analysis of C,H,N (and halogens if present), infrared, N.M.R. and U.V. spectra.

EXAMPLE 1

4-(4-fluorophenyl)-5-[2-(4-(2-methoxyphenyl)-1-piperazinyl)ethyl]-1,3-dioxol-2-one dihydrochloride A solution of 20 g of 1-p-fluorobenzoyl-1-hydroxy-3-(4-(2-methoxyphenyl)-1-piperazinyl)propane in 200 cc of anhydrous chloroform is added in 60 minutes to 33 ml of a 20% phosgene solution in toluene, stirred and cooled to 0° C.

The reaction mixture is stirred at room temperatura for one hour, then refluxed for 6 hours. It is cooled to room temperature, the solid is filtered, then dissolved under heating in 300 ml of alcohol, and 15 ml of alcoholic HCl are added. The solution is then cooled and filtered. M.p.=238°–40° C. (from alcohol)

The same compound is obtained by substituting phosgene by trichloromethyl chlorocarbonate.

Similarly the preparation of the following compound is carried out:

4-(4-fluorophenyl)-5-[2-diethylaminoethyl]-1,3-dioxol-2-one hydrochloride m.p.=159°–61° C. (from ethanol)

4-(4-fluorophenyl)-5-[2-(4-phenyl-1-piperazinyl)ethyl]-1,3-dioxol-2-one dihydrochloride m.p.=264°–5° C. (from ethanol)

4-(4-fluorophenyl)-5-[2-(N-methyl-N-2-phenylethylamino)ethyl]-1,3-dioxol-2-one hydrochloride m.p.=166°–8° C. (from isopropanol)

4-(4-fluorophenyl)-5-[2-(4-(2-pyridyl)-1-piperazinyl)ethyl]-1,3-dioxol-2-one dihydrochloride m.p.=265°–7° C. (from ethanol)

4-(4-fluorophenyl)-5-[2-(4-methyl-1-piperazinyl)ethyl]-1,3-dioxol-2-one dihydrochloride m.p.=279° C. (from ethanol)

4-(4-fluorophenyl)-5-[2-(7,12-dioxo-3-azaspiro[5,6]dodec-3-yl)ethyl]-1,3-dioxol-2-one hydrochloride m.p.=211°–3° C. (from ethanol)

4-(4-chlorophenyl)-5-[2-(4-phenyl-1-piperazinyl)ethyl]-1,3-dioxol-2-one dihydrochloride m.p.=262°–5° C. (from ethanol)

4-(4-fluorophenyl)-5-[2-(4-(4-chlorophenyl)-1-(1,2,3,6-tetrahydropyridyl))ethyl]-1,3-dioxol-2-one hydrochloride m.p.=220° C. (from methanol)

4-(4-fluorophenyl)-5-[2-(1-morpholinyl)ethyl]-1,3-dioxol-2-one hydrochloride m.p.=188°–90° C. (from ethanol)

4-(4-tolyl)-5-[2-(4-phenyl-1-piperazinyl)ethyl]-1,3-dioxol-2-one hydrochloride m.p.=252°–4° C. (from ethanol)

4-(4-fluorophenyl)-5-[2-(4-(3,5-dichlorophenyl)-1-piperazinyl)ethyl]-1,3-dioxol-2-one hydrochloride m.p.=277°–9° C. (from ethanol 4-(4-fluorophenyl)-5-[2-(4-(4-chlorophenyl)-3-methyl-1-piperazinyl)ethyl]-1,3-dioxol-2-one dihydrochloride m.p.=228°–30° C. (from ethanol)

4-(4-fluorophenyl)-5-[2-(4-(2,5-dichlorophenyl)-1-piperazinyl)ethyl]-1,3-dioxol-2-one hydrochloride m.p.=240°–2° C. (from ethanol)

4-(4-fluorophenyl)-5-[2-(4-(3,4-dichlorophenyl)-1-piperazinyl)ethyl]-1,3-dioxol-2-one hydrochloride m.p.=228°–30° C. (from ethanol)

4-(2-naphtyl)-5-[2-(4-phenyl-1-piperazinyl)ethyl]-1,3-dioxol-2-one hydrochloride m.p.=239°–40° C. (from ethanol)

4-(4-methoxyphenyl)-5-[2-(4-phenyl-1-piperazinyl)ethyl]-1,3-dioxol-2-one dihydrochloride m.p.=256°–8° C. (from ethanol)

4-(4-methylthiophenyl)-5-[2-(4-phenyl-1-piperazinyl)ethyl]-1,3-dioxol-2-one dihydrochloride m.p.=255° C. (from ethanol)

4-(4-fluorophenyl)-5-[2-(3-azaspiro[5,5]undecan-3-yl)ethyl]-1,3-dioxol-2-one hydrochloride m.p.=270°–2° C. (from ethanol)

4-(4-chlorophenyl)-5-[2-(4-(4-chlorobenzhydryl)-1-piperazinyl)ethyl]-1,3-dioxol-2-one dihydrochloride m.p.=242°–43° C. (from ethanol)

4-(4-biphenyl)-5-[2-(4-phenyl-1-piperazinyl)ethyl]-1,3-dioxol-2-one dihydrochloride m.p.=242°–43° C. (from ethanol)

4-(4-fluorophenyl)-5-[2-(4-($\alpha,\alpha,\alpha$-trifluoro-3-tolyl)-1-piperazinyl)ethyl]-1,3-dioxol-2-one hydrochloride m.p.=194°–196° C. (from ethanol)

4-(4-chlorophenyl)-5-[2-(4-(2-pyrimidinyl)-1-piperazinyl)ethyl]1,3-dioxol-2-one maleate m.p.=162°–5° C. (from ethanol)

4-(4-fluorophenyl)-5-[2-(4-(3-chlorophenyl-1-piperazinyl)ethyl]-1,3-dioxol-2-one dihydrochloride m.p.=200°–205° C. (from ethanol)

4-(4-fluorophenyl)-5-[3-(4-phenyl-1-piperazinyl)propyl]-1,3-dioxol-2-one hydrochloride m.p.=175°–180° C. (from ethanol) 4-(4-chlorophenyl)-5-[2-(4-(4-chlorophenyl)-1-piperazinyl)ethyl]-1,3-dioxol-2-one hydrochloride m.p.=251°–2° C. (from ethanol)

4-(4-chlorophenyl)-5-[2-(4-phenyl-1-piperidinyl)ethyl]-1,3-dioxol-2-one hydrochloride m.p.=242°-3° C. (from ethanol)

4-(4-chlorophenyl)-5-[2-(4-benzhydryl-1-piperazinyl)ethyl]-1,3-dioxol-2-one hydrochloride m.p.=159°-60° C. (from ethanol)

4-(4-fluorophenyl)-5-[2-(1-piperidinyl)ethyl]-1,3-dioxol-2-one hydrochloride m.p.=181°-2° C. (from ethanol)

4-(4-fluorophenyl)-5-[2-(N-methyl-N-cyclohexylamino)ethyl]-1,3-dioxol-2-one hydrochloride m.p.=203°-4° C. (from ethanol)

4-(4-chlorophenyl)-5-[2-(4-phenylmethyl-1-piperazinyl)ethyl]-1,3-dioxol-2-one dihydrochloride m.p.=275°-6° C. (from dimethylformamide).

The 1-aroyl-1-hydroxy-3-aminopropanes are obtained as described in C.A. 80, 27292 k (1974).

EXAMPLE 2

4-Phenyl-5-[2-(4-phenyl-1-piperazinyl)ethyl]-1,3-dioxol-2-one dihydrochloride

A solution of 2,5 g of 1-benzoyl-1-hydroxy-3-(4-phenyl-1-piperazinyl)propane and 5 g of 1,1'-carbonyldiimidazole in 100 ml of anhydrous benzene is refluxed for 8 hours. The reaction mixture is repeatedly washed with water, dried on $Na_2SO_4$ and evaporated to dryness at reduced pressure.

The residue is transformed into the corresponding dihydrochloride.

M.p.=246°-8° C. (from alcohol).

We claim:

1. A 4-aryl-5-aminoalkyl-1,3-dioxol-2-one, having general formula (I)

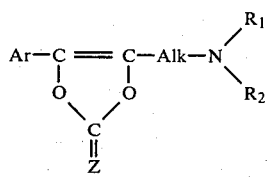

(I)

wherein: Ar is a residue selected from the group consisting of (a) phenyl, (b) phenyl substituted by a member selected from the group consisting of lower alkyl, lower alkoxy, halogen and lower alkylmercapto, (c) biphenyl, and (d) naphthyl; Alk is a saturated chain of one to three carbon atoms;

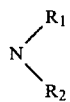

is the residue of piperazine and piperazine substituted in the 4-position with (a) alkyl, (b) phenyl, (c) diphenylalkyl, (d) halophenyl, (e) halodiphenylalkyl, (f) alkoxyphenyl, (g) alkoxydiphenyl, (h) pyridyl, (i) pyrimidinyl, (j) trifluoromethylphenyl and Z is oxygen and pharmaceutically acceptable salts thereof.

2. A compound according to claim 1 which is 4-(4-fluorophenyl)-5-[2-(4-(2-methoxyphenyl)-1-piperazinyl)ethyl]-1,3-dioxol-2-one, and its pharmaceutically acceptable acid addition salts.

3. A compound according to claim 1 which is 4-(4-fluorophenyl)-5-[2-(4-phenyl-1-piperazinyl)ethyl]-1,3-dioxol-2-one, and its pharmaceutically acceptable acid addition salts.

4. A compound according to claim 1 which is 4-(4-fluorophenyl)-5-[2-(4-(2-pyridyl)-1-piperazinyl)ethyl]-1,3-dioxol-2-one, and its pharmaceutically acceptable acid addition salts.

5. A compound according to claim 1 which is 4-(4-fluorophenyl)-5-[2-(4-methyl-1-piperazinyl)-ethyl]-1,3-dioxol-2-one, and its pharmaceutically acceptable acid addition salts.

6. A compound according to claim 1 which is 4-(4-chlorophenyl)-5-[2-(4-phenyl-1-piperazinyl)-ethyl]-1,3-dioxol-2-one, and its pharmaceutically acceptable acid addition salts.

7. The compound according to claim 1 which is 4-(4-tolyl)-5-[2-(4-phenyl-1-piperazinyl)ethyl]-1,3-dioxol-2-one, and its pharmaceutically acceptable acid addition salts.

8. A compound according to claim 1 which is 4-(4-fluorophenyl)-5-[2-(4-(3,5-dichlorophenyl)-1-piperazinyl)ethyl]-1,3-dioxol-2-one, and its pharmaceutically acceptable acid addition salts.

9. A compound according to claim 1 which is 4-(4-fluorophenyl)-5-[2-(4-(4-chlorophenyl)-3-methyl-1-piperazinyl)ethyl]-1,3-dioxol-2-one, and its pharmaceutically acceptable acid addition salts.

10. A compound according to claim 1 which is 4-(4-fluorophenyl)-5-[2-(4-(2,5-dichlorophenyl)-1-piperazinyl)ethyl]-1,3-dioxol-2-one, and its pharmaceutically acceptable acid addition salts.

11. A compound according to claim 1 which is 4-(4-fluorophenyl)-5-[2-(4-(3,4-dichlorophenyl)-1-piperazinyl)ethyl]-1,3-dioxol-2-one, and its pharmaceutically acceptable acid addition salts.

12. A compound according to claim 1 which is 4-(2-naphtyl)-5-[2-(4-phenyl-1-piperazinyl)ethyl]-1,3-dioxol-2-one, and its pharmaceutically acceptable acid addition salts.

13. A compound according to claim 1 which is 4-(4-metoxyphenyl)-5-[2-(4-phenyl-1-piperazinyl)ethyl]-1,3-dioxol-2-one, and its pharmaceutically acceptable acid addition salts.

14. A compound according to claim 1 which is 4-(4-methylthiophenyl)-5-[2-(4-phenyl-1-piperazinyl)ethyl]-1,3-dioxol-2-one, and its pharmaceutically acceptable acid addition salts.

15. A compound according to claim 1 which is 4-(4-chlorophenyl)-5-[2-(4-(4-chlorobenzhydryl)-1-piperazinyl)ethyl]-1,3-dioxol-2-one, and its pharmaceutically acceptable acid addition salts.

16. A compound according to claim 1 which is 4-(4-biphenyl)-5-[2-(4-phenyl-1-piperazinyl)ethyl]-1,3-dioxol-2-one, and its pharmaceutically acceptable acid addition salts.

17. A compound according to claim 1 which is 4-(4-fluorophenyl)-5-[2-(4-(α,α,α-trifluoro-3-tolyl)-1-piperazinyl)ethyl]-1,3-dioxol-2-one, and its pharmaceutically acceptable acid addition salts.

18. A compound according to claim 1 which is 4-(4-chlorophenyl)-5-[2-(4-(2-pyrimidinyl)-1-piperazinyl)ethyl]-1,3-dioxol-2-one, and its pharmaceutically acceptable acid addition salts.

19. A compound according to claim 1 which is 4-(4-fluorophenyl)-5-[2-(4-(3-chlorophenyl)-1-piperazinyl)ethyl]-1,3-dioxol-2-one, and its pharmaceutically acceptable acid addition salts.

20. A compound according to claim 1 which is 4-(4-fluorophenyl)-5-[3-(4-phenyl-1-piperazinyl)-propyl]-1,3-dioxol-2-one, and its pharmaceutically acceptable acid addition salts.

21. A compound according to claim 1 which is 4-phenyl-5-[2-(4-phenyl-1-piperazinyl)ethyl]-1,3-dioxol-2-one, and its pharmaceutically acceptable acid addition salts.

22. A compound according to claim 1 which is 4-(4-chlorophenyl)-5-[2-(4-(4-chlorophenyl)-1-piperazinyl)ethyl]-1,3-dioxol-2-one, and its pharmaceutically acceptable acid addition salts.

23. A compound according to claim 1 which is 4-(4-chlorophenyl)-5-[2-(4-benzhydryl-1-piperazinyl)ethyl]-1,3-dioxol-2-one, and its pharmaceutically acceptable acid addition salts.

24. A compound according to claim 1 which is 4-(4-chlorophenyl)-5-[2-(4-phenylmethyl-1-piperazinyl)ethyl]-1,3-dioxol-2-one, and its pharmaceutically acceptable acid addition salts.

25. A pharmaceutical composition with hypocholesterolemic, hypolipemic, antiulcer, antihistaminic and antiserotoninic activity, which contains an effective amount of at least one 4-aryl-5-aminoalkyl-1,3-dioxol-2-one, having general formula (I)

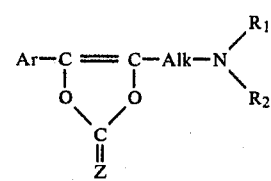

wherein: Ar is a residue selected from the group consisting of (a) phenyl, (b) phenyl substituted by a member selected from the group consisting of lower alkyl, lower alkoxy, halogen, and lower alkylmercapto, (c) biphenyl and (d) naphthyl; Alk is a saturated chain of one to three carbon atoms;

is the residue of piperazine and piperazine substituted in the 4-position with (a) alkyl, (b) phenyl, (c) diphenylalkyl, (d) halophenyl, (e) halodiphenylalkyl, (f) alkoxyphenyl, (g) alkoxydiphenyl, (h) pyridyl, (i) pyrimidinyl, (j) trifluoromethylphenyl
and Z is oxygen
or a pharmaceutically acceptable salt thereof in association with a suitable pharmaceutical carrier.

* * * * *